United States Patent
Chun et al.

(10) Patent No.: US 10,023,887 B2
(45) Date of Patent: Jul. 17, 2018

(54) METHOD OF MANUFACTURING AN AMINO-ACID COMPOSITION USING ANIMAL BY-PRODUCTS

(71) Applicants: Esther Miyeon Chun, Yongin-si (KR); John Yohan Chun, Irvine, CA (US)

(72) Inventors: Esther Miyeon Chun, Yongin-si (KR); John Yohan Chun, Irvine, CA (US)

( * ) Notice: Subject to any disclaimer, the term of this patent is extended or adjusted under 35 U.S.C. 154(b) by 24 days.

(21) Appl. No.: 15/158,021

(22) Filed: May 18, 2016

(65) Prior Publication Data

US 2017/0275658 A1 Sep. 28, 2017

(30) Foreign Application Priority Data

Mar. 25, 2016 (KR) .................. 10-2016-0035862

(51) Int. Cl.
*C12P 13/04* (2006.01)
*A23L 1/305* (2006.01)
*A61L 2/20* (2006.01)
*C05F 1/00* (2006.01)

(52) U.S. Cl.
CPC .............. *C12P 13/04* (2013.01); *A23L 1/305* (2013.01); *A61L 2/202* (2013.01); *C05F 1/005* (2013.01); *Y02P 20/145* (2015.11)

(58) Field of Classification Search
None
See application file for complete search history.

(56) References Cited

U.S. PATENT DOCUMENTS

| | | | | | |
|---|---|---|---|---|---|
| 4,308,293 | A | * | 12/1981 | Tribble | A01N 61/00 424/725.1 |
| 7,001,519 | B2 | * | 2/2006 | Linden | A01K 63/04 119/227 |
| 2011/0158926 | A1 | * | 6/2011 | Dal Farra | A61K 8/345 424/62 |
| 2013/0211113 | A1 | * | 8/2013 | Eckelberry | C11B 3/005 554/1 |

FOREIGN PATENT DOCUMENTS

| | | |
|---|---|---|
| KR | 10-2008-0040296 A | 5/2008 |
| KR | 10-0936626 B | 1/2010 |
| KR | 10-2011-0017742 A | 2/2011 |
| KR | 10-1100329 B | 12/2011 |
| KR | 10-2013-0044098 A | 5/2013 |
| KR | 10-2015-0143903 A | 12/2015 |
| KR | 10-1586768 B | 1/2016 |

* cited by examiner

*Primary Examiner* — Jennifer M. H. Tichy
(74) *Attorney, Agent, or Firm* — Merchant & Gould P.C.

(57) ABSTRACT

The present disclosure provides a method for preparing an amino acid composition using an animal byproduct, particularly a method for obtaining an amino acid composition of high quality using an animal byproduct more effectively in short time. Because an amino acid composition can be obtained from an animal byproduct more effectively and quickly using the method of the present disclosure, utilization of livestock waste, etc. can be enhanced and application as various products can be expected.

7 Claims, 4 Drawing Sheets

TYPE 1        TYPE 2        TYPE 3 ically describes a process of preparing an
METHOD OF MANUFACTURING AN AMINO-ACID COMPOSITION USING ANIMAL BY-PRODUCTS

CROSS-REFERENCE TO RELATED APPLICATION

This application claims the priority of Korean Patent Application No. 10-2016-0035862, filed on Mar. 25, 2016, and all the benefits accruing therefrom under 35 U.S.C. § 119, the contents of which in its entirety are herein incorporated by reference.

BACKGROUND

1. Field

The present disclosure relates to a method for preparing an amino acid composition using an animal byproduct, etc.

2. Description of the Related Art

Meat such as beef, pork, chicken, etc. is the edible part of the corresponding animal which has been bred and slaughtered for use as food. A variety of byproducts including hair, blood, leather, guts, placenta, claws and other non-edible parts are produced from the slaughterhouse.

Most of the byproducts are disposed of as wastes except for some of them which are used as food. The leather is also buried or incinerated mostly except for very little processed as natural leather. Recently, various solutions are proposed for treatment of the animal byproducts with the growing social concerns about environmental pollution. However, the proposed solutions are costly and inefficient.

In another aspect, the animal byproducts can be utilized as useful resources because they are rich in proteins and other nutrients. However, because the animal byproducts are mostly disposed of as wastes without being fully utilized, adequate methods for utilizing the animal byproducts are necessary. There has been an attempt to prepare liquid fertilizer using the blood of slaughtered animals. Reference can be made to Korean Patent Registration No. 10-0936626.

However, the method described in the patent document is disadvantageous in that it takes a lot of time to process the blood of slaughtered animals and the efficiency is low.

The inventors of the present disclosure have conducted researches to solve the above-described problems and have invented a method for obtaining amino acids from animal byproducts more effectively.

REFERENCES OF THE RELATED ART

Patent Documents (Patent document 1) Korean Patent Registration No. KR10-0936626 (Jan. 5, 2010).

SUMMARY

The present disclosure is directed to providing a method for obtaining an amino acid composition of high quality from animal byproducts more effectively in short time.

In an aspect, the present disclosure provides a method for preparing an amino acid composition using an animal byproduct, which comprises:

(1) a step of disrupting the cell membrane of an animal byproduct;

(2) a step of obtaining a fermentation product by fermenting the byproduct with the cell membrane disrupted; and (3) a step of sterilizing the fermentation product.

In another aspect, the present disclosure provides a product comprising an animal byproduct-derived amino acid composition, which comprises 15-25 wt % of animal byproduct-derived total free amino acids, 1-4 wt % of animal byproduct-derived aspartic acid, 1-4 wt % of animal byproduct-derived glutamic acid, 0.5-3 wt % of animal byproduct-derived alanine, 1-4 wt % of animal byproduct-derived leucine and 1-3 wt % of animal byproduct-derived lysine based on the total weight of the animal byproduct-derived amino acid composition.

The animal may comprise livestock and fish.

Because an amino acid composition can be obtained from an animal byproduct more effectively and quickly using the method of the present disclosure, utilization of livestock waste, etc. can be enhanced and application as various products can be expected. In addition, environmental pollution can be resolved and social cost can be saved.

DETAILED DESCRIPTION

In the present disclosure, an "amino acid composition" refers to a composition which comprises a single or various kinds of amino acid(s) and, optionally, other ingredients.

In the present disclosure, a "nanobubble generator" refers to a bubble-generating apparatus for transferring a gas to a liquid by artificially injecting fine bubbles into the liquid. More specifically, it refers to an apparatus which generates a liquid in which nanosized nanobubbles are mixed via a process of sucking and then spouting the liquid.

In an aspect, the present disclosure relates to a method for preparing an amino acid composition using an animal byproduct.

In an aspect, the present disclosure relates to a method for preparing an amino acid composition using an animal byproduct, which comprises:

(1) a step of disrupting the cell membrane of an animal byproduct;

(2) a step of obtaining a fermentation product by fermenting the byproduct with the cell membrane disrupted; and (3) a step of sterilizing the fermentation product.

In an aspect of the present disclosure, the animal byproduct in the step (1) comprises the skin, muscle, blood and guts of livestock. In another aspect, the animal may comprise fish and the guts may comprise the placenta.

In an aspect of the present disclosure, the step (1) of disrupting the cell membrane may comprise one or more selected from a group consisting of a process of crushing, a process of adding purified water, a process of adding purified water comprising an alkaline substance and a process of adding lye prepared from wood ash. In another aspect of the present disclosure, the alkaline substance may be either a strong base or a weak base. Specifically, it may be NaOH or KOH. A mixing ratio of the strong base or the weak base is not limited. Specifically, when NaOH or KOH is used, it may be used in an amount of 10% wt based on 1 kg of the purified water. The lye prepared from wood ash is not specifically limited, but may be a solution obtained by adding 10% wt of ash powder prepared by burning a deciduous or coniferous tree based on 1 kg of purified water and extracting for 10 days.

In an aspect of the present disclosure, the step of disrupting the cell membrane may further comprise, after or during one or more selected from a group consisting of a process of crushing, a process of adding purified water, a process of adding purified water comprising an alkaline substance and a process of adding lye prepared from wood ash, a process of controlling pH.

In an aspect of the present disclosure, the step of disrupting the cell membrane may further comprise, after or during one or more selected from a group consisting of a process of crushing, a process of adding purified water, a process of adding purified water comprising an alkaline substance and a process of adding lye prepared from wood ash, a process of controlling temperature.

In an aspect of the present disclosure, there may be no limitation in the order of the process of controlling pH and the process of controlling temperature.

In an aspect of the present disclosure, the crushing process may comprise a process of using a homogenizer, a process of using stirring and rotation, a process of explosion, a process of sonication, a process of using a nanobubble generator, a process of cooling, etc. Specifically, it may comprise a process of using a nanobubble generator.

In an aspect of the present disclosure, an amount of the purified water, the purified water comprising an alkaline substance or the lye prepared from wood ash may be 5-15 wt % based on the total weight of the byproduct.

In an aspect of the present disclosure, the amount of the purified water, the purified water comprising an alkaline substance or the lye prepared from wood ash may be 1 wt % or more, 2 wt % or more, 3 wt % or more, 4 wt % or more, 5 wt % or more, 6 wt % or more, 7 wt % or more, 8 wt % or more, 9 wt % or more, 10 wt % or more, 11 wt % or more, 12 wt % or more, 13 wt % or more, 14 wt % or more, 15 wt % or more, 16 wt % or more, 17 wt % or more, 18 wt % or more, 19 wt % or more, 20 wt % or more, 25 wt % or more, 30 wt % or more, 35 wt % or more, 40 wt % or more, 50 wt % or more, 60 wt % or more or 70 wt % or more or 1 wt % or less, 2 wt % or less, 3 wt % or less, 4 wt % or less, 5 wt % or less, 6 wt % or less, 7 wt % or less, 8 wt % or less, 9 wt % or less, 10 wt % or less, 11 wt % or less, 12 wt % or less, 13 wt % or less, 14 wt % or less, 15 wt % or less, 16 wt % or less, 17 wt % or less, 18 wt % or less, 19 wt % or less, 20 wt % or less, 25 wt % or less, 30 wt % or less, 35 wt % or less, 40 wt % or less, 50 wt % or less, 60 wt % or less or 70 wt % or less, specifically 3-18 wt %, more specifically 5-15 wt %, further more specifically 10 wt %, based on the total weight of the byproduct.

In an aspect of the present disclosure, the pH may be controlled to be maintained at 5-7.

In an aspect of the present disclosure, the pH may be controlled to be maintained at 1 or higher, 2 or higher, 3 or higher, 4 or higher, 5 or higher, 5.5 or higher, 5.6 or higher, 5.7 or higher, 5.8 or higher, 5.9 or higher, 6 or higher, 6.1 or higher, 6.2 or higher, 6.3 or higher, 6.4 or higher, 6.5 or higher, 7 or higher, 8 or higher, 9 or higher, 10 or higher, 11 or higher, or 12 or higher or 1 or lower, 2 or lower, 3 or lower, 4 or lower, 5 or lower, 5.5 or lower, 5.6 or lower, 5.7 or lower, 5.8 or lower, 5.9 or lower, 6 or lower, 6.1 or lower, 6.2 or lower, 6.3 or lower, 6.4 or lower, 6.5 or lower, 7 or lower, 8 or lower, 9 or lower, 10 or lower, 11 or lower, 12 or lower or 13 or lower, specifically 5-7, more specifically 5.7-6.1, further more specifically 5.9.

In an aspect of the present disclosure, the temperature may be controlled to be 52-65° C.

In an aspect of the present disclosure, temperature may be controlled to be 30° C. or higher, 35° C. or higher, 40° C. or higher, 45° C. or higher, 47° C. or higher, 49° C. or higher, 50° C. or higher, 51° C. or higher, 52° C. or higher, 53° C. or higher, 54° C. or higher, 55° C. or higher, 57° C. or higher, 60° C. or higher, 62° C. or higher, 65° C. or higher, 67° C. or higher, 70° C. or higher or 75° C. or higher or 30° C. or lower, 35° C. or lower, 40° C. or lower, 45° C. or lower, 47° C. or lower, 49° C. or lower, 50° C. or lower, 51° C. or lower, 52° C. or lower, 53° C. or lower, 54° C. or lower, 55° C. or lower, 57° C. or lower, 60° C. or lower, 62° C. or lower, 65° C. or lower, 67° C. or lower, 70° C. or lower or 75° C. or lower, specifically 52-65° C.

In an aspect of the present disclosure, the fermentation in the step (2) may comprise being performed by mixing with an enzyme. The enzyme refers to a substance such as a protein, etc. involved in chemical reactions in vivo. During the reaction, the enzyme is temporarily bound to a substrate to form an enzyme-substrate complex and acts as a catalyst. The produced reaction product is separated from the enzyme. The enzyme exhibits enzymatic specificity of permitting only a specific substrate molecule with unique three-dimensional amino acid structure and electrochemical properties corresponding to its active site. The rate of an enzymatic reaction is proportional to the concentration of the substrate and reaches the maximum rate when all the active sites on the enzyme surface are completely filled with the substrate. The enzymatic action is inhibited by competitive inhibition, non-competitive inhibition, etc. The non-competitive inhibition also comprises allosteric inhibition. The inventors of the present disclosure have investigated many enzymes for maximizing the rate of enzymatic reaction in consideration of the characteristics of the enzymes as well as the crushing, acidity and freshness of the substrate. As a result, they have prepared single enzymes or mixtures of enzymes that allow fermentation in short time.

In an aspect of the present disclosure, the enzyme may comprise one or more selected from a group consisting of proteinase, protease, pepsin, rennin, trypsin, chymotrypsin, erepsin, aminopeptidase, prolinase, prolidase, enterokinase, peptidase, carboxypeptidase, dipeptidase, papain, bromelain, ficin, actinidain, elastase, subtilisin, pancreatin, nattokinase, arazyme, collagenase, keratinase, gelatinase, savinase, alkaline protease, subclasses thereof, an enzyme usually used in food processing, an enzyme usually used in preparation of fertilizers, an enzyme usually used in preparation of food additives, a commercially available common protein hydrolase and an enzyme usually used in preparation of feed.

In an aspect of the present disclosure, the enzyme may be a mixture of several enzymes that can be used in fertilizers, food, food additives, etc. and can ferment or degrade proteins, fats, carbohydrates, etc.

In an aspect of the present disclosure, the enzyme or enzyme mixture may be mixed in an amount of 1 wt % or more, 1.5 wt % or more, 2 wt % or more, 2.5 wt % or more, 3 wt % or more, 3.5 wt % or more, 4 wt % or more, 4.5 wt % or more, 5 wt % or more, 5.5 wt % or more, 6 wt % or more, 6.5 wt % or more, 7 wt % or more, 8 wt % or more, 9 wt % or more, 10 wt % or more, 11 wt % or more, 12 wt % or more, 13 wt % or more, 14 wt % or more, 15 wt % or more, 16 wt % or more, 17 wt % or more, 18 wt % or more, 19 wt % or more, 20 wt % or more or 30 wt % or more or 1 wt % or less, 1.5 wt % or less, 2 wt % or less, 2.5 wt % or less, 3 wt % or less, 3.5 wt % or less, 4 wt % or less, 4.5 wt % or less, 5 wt % or less, 5.5 wt % or less, 6 wt % or less, 6.5 wt % or less, 7 wt % or less, 8 wt % or less, 9 wt % or less, 10 wt % or less, 11 wt % or less, 12 wt % or less, 13 wt % or less, 14 wt % or less, 15 wt % or less, 16 wt % or less, 17 wt % or less, 18 wt % or less, 19 wt % or less, 20 wt % or less or 30 wt % or less, specifically 2.5-4.5 wt %, more specifically 3.5 wt %, based on the total weight of the byproduct to which the purified water, the purified water comprising an alkaline substance or the lye prepared from wood ash has been added.

In an aspect of the present disclosure, the mixing may be performed under a condition where the temperature of the byproduct which has passed the step (1) is 0-30° C.

In an aspect of the present disclosure, the mixing with the enzyme may be performed when the temperature of the byproduct which has passed the step (1) is −25° C. or higher, −20° C. or higher, −15° C. or higher, −10° C. or higher, −6° C. or higher, −3° C. or higher, −1° C. or higher, 0° C. or higher, 3° C. or higher, 4° C. or higher, 5° C. or higher, 6° C. or higher, 7° C. or higher, 8° C. or higher, 9° C. or higher, 10° C. or higher, 11° C. or higher, 12° C. or higher, 15° C. or higher, 18° C. or higher, 20° C. or higher, 21° C. or higher, 24° C. or higher, 28° C. or higher, 32° C. or higher or 35° C. or higher or −25° C. or lower, −20° C. or lower, −15° C. or lower, −10° C. or lower, −6° C. or lower, −3° C. or lower, −1° C. or lower, 0° C. or lower, 3° C. or lower, 4° C. or lower, 5° C. or lower, 6° C. or lower, 7° C. or lower, 8° C. or lower, 9° C. or lower, 10° C. or lower, 11° C. or lower, 12° C. or lower, 15° C. or lower, 18° C. or lower, 20° C. or lower, 21° C. or lower, 24° C. or lower, 28° C. or lower, 32° C. or lower or 35° C. or lower, specifically 5-25° C., more specifically 15-25° C.

In an aspect of the present disclosure, the method may further comprise, after the mixing with the enzyme, a process of controlling the temperature of the byproduct to which the enzyme has been added.

In an aspect of the present disclosure, the temperature may be controlled to be 30° C. or higher, 35° C. or higher, 40° C. or higher, 45° C. or higher, 47° C. or higher, 49° C. or higher, 50° C. or higher, 51° C. or higher, 52° C. or higher, 53° C. or higher, 54° C. or higher, 55° C. or higher, 57° C. or higher, 60° C. or higher, 61° C. or higher, 62° C. or higher, 63° C. or higher, 64° C. or higher, 65° C. or higher, 66° C. or higher, 67° C. or higher, 68° C. or higher, 70° C. or higher or 75° C. or higher or 30° C. or lower, 35° C. or lower, 40° C. or lower, 45° C. or lower, 47° C. or lower, 49° C. or lower, 50° C. or lower, 51° C. or lower, 52° C. or lower, 53° C. or lower, 54° C. or lower, 55° C. or lower, 57° C. or lower, 60° C. or lower, 61° C. or lower, 62° C. or lower, 63° C. or lower, 64° C. or lower, 65° C. or lower, 66° C. or lower, 67° C. or lower, 68° C. or lower, 70° C. or lower or 75° C. or lower, specifically 52-65° C.

In an aspect of the present disclosure, the step (2) of obtaining the fermentation product may comprise a stirring step.

In an aspect of the present disclosure, the stirring may be performed at 20 rpm or higher, 25 rpm or higher, 30 rpm or higher, 35 rpm or higher, 40 rpm or higher, 45 rpm or higher, 50 rpm or higher, 55 rpm or higher, 60 rpm or higher, 65 rpm or higher, 70 rpm or higher, 75 rpm or higher, 80 rpm or higher, 85 rpm or higher, 90 rpm or higher, 95 rpm or higher, 100 rpm or higher, 110 rpm or higher or 120 rpm or higher or 20 rpm or lower, 25 rpm or lower, 30 rpm or lower, 35 rpm or lower, 40 rpm or lower, 45 rpm or lower, 50 rpm or lower, 55 rpm or lower, 60 rpm or lower, 65 rpm or lower, 70 rpm or lower, 75 rpm or lower, 80 rpm or lower, 85 rpm or lower, 90 rpm or lower, 95 rpm or lower, 100 rpm or lower, 110 rpm or lower or 120 rpm or lower, specifically 50-70 rpm, more specifically 60 rpm.

In an aspect of the present disclosure, the sterilizing in the step (3) may comprise sterilizing with ozone, although not being limited thereto. A commonly used existing sterilizing method may also be used. For example, a pasteurization method of heating at 70° C. for 30 minutes and then cooling slowly, a UV sterilization method of exposing to UV for a predetermined time, etc. may be used.

In an aspect of the present disclosure, the method may further comprise, after the step (3), a step of adding a preservative.

In an aspect of the present disclosure, an extract of a plant comprising natural preservative ingredient may be used as the preservative. Specifically, it may comprise mugwort, plantain, aloe, peony, grapefruit and wood vinegar (prepared by condensing steam generated during carbonization of wood; easily commercially available), although not being limited thereto. Specifically, the preservative may be one obtained by mixing a solution prepared by adding 2% of mugwort, plantain, aloe, peony or grapefruit to purified water based on the weight of the purified water and extracting the same by heating and wood vinegar at a ratio of 1:1.

In an aspect of the present disclosure, the preservative may be added in an amount of 1-10 wt % based on the total weight of the byproduct to which the purified water, the purified water comprising an alkaline substance or the lye prepared from wood ash has been added.

In an aspect of the present disclosure, the preservative may be added in an amount of 1 wt % or more, 2 wt % or more, 3 wt % or more, 4 wt % or more, 5 wt % or more, 6 wt % or more, 7 wt % or more, 8 wt % or more, 9 wt % or more, 10 wt % or more, 11 wt % or more, 12 wt % or more, 13 wt % or more, 14 wt % or more, 15 wt % or more, 18 wt % or more, 20 wt % or more, 25 wt % or more or 30 wt % or more or 1 wt % or less, 2 wt % or less, 3 wt % or less, 4 wt % or less, 5 wt % or less, 6 wt % or less, 7 wt % or less, 8 wt % or less, 9 wt % or less, 10 wt % or less, 11 wt % or less, 12 wt % or less, 13 wt % or less, 14 wt % or less, 15 wt % or less, 18 wt % or less, 20 wt % or less, 25 wt % or less or 30 wt % or less, specifically 3-7 wt % or 4-6 wt %, more specifically 5 wt % or 5.1 wt %, based on the total weight of the byproduct to which the purified water, the purified water comprising an alkaline substance or the lye prepared from wood ash has been added.

In an aspect, the present disclosure may relate to a product comprising an animal byproduct-derived amino acid composition, which comprises 15-25 wt % of animal byproduct-derived total free amino acids, 1-4 wt % of animal byproduct-derived aspartic acid, 1-4 wt % of animal byproduct-derived glutamic acid, 1-4 wt % of animal byproduct-derived alanine, 1-4 wt % of animal byproduct-derived leucine and 1-4 wt % of animal byproduct-derived lysine based on the total weight of the animal byproduct-derived amino acid composition.

In another aspect of the present disclosure, the animal byproduct-derived amino acid composition may comprise the total free amino acids in an amount of 10 wt % or more, 12 wt % or more, 14 wt % or more, 15 wt % or more, 16 wt % or more, 17 wt % or more, 18 wt % or more, 19 wt % or more, 20 wt % or more, 21 wt % or more, 22 wt % or more, 23 wt % or more, 24 wt % or more, 25 wt % or more, 27 wt % or more, 30 wt % or more or 35 wt % or more or 35 wt % or less, 27 wt % or less, 25 wt % or less, 24 wt % or less, 23 wt % or less, 22 wt % or less, 21 wt % or less, 20 wt % or less, 19 wt % or less, 18 wt % or less, 17 wt % or less, 16 wt % or less, 15 wt % or less, 14 wt % or less, 12 wt % or less or 10 wt % or less, specifically 15-25 wt %, more specifically 20.84 wt %, based on the total weight of the composition.

In another aspect of the present disclosure, the animal byproduct-derived amino acid composition may comprise each of aspartic acid, glutamic acid, alanine, leucine and lysine in an amount of 0.1 wt % or more, 0.3 wt % or more, 0.5 wt % or more, 0.7 wt % or more, 0.9 wt % or more, 1 wt % or more, 2 wt % or more, 3 wt % or more, 4 wt % or more, 5 wt % or more, 6 wt % or more, 7 wt % or more or 10 wt % or more or 10 wt % or less, 9 wt % or less, 8 wt % or less, 7 wt % or less, 6 wt % or less, 5 wt % or less, 4 wt % or less, 3 wt % or less, 2 wt % or less, 1 wt % or less, 0.9 wt % or less, 0.7 wt % or less, 0.5 wt % or less, 0.3 wt % or less or 0.1 wt % or less, based on the total weight of the composition. Specifically, it may comprise 1.5-3.5 wt % of aspartic acid, 1-3 wt % of glutamic acid, 0.5-3 wt % of alanine, 2-4 wt % of leucine and 1-3 wt % lysine, more specifically 2.47 wt % of aspartic acid, 1.92 wt % of glutamic acid, 1.71 wt % of alanine, 2.81 wt % of leucine and 2.15 wt % of lysine.

In an aspect of the present disclosure, the animal byproduct-derived amino acid composition may be an animal byproduct-derived amino acid composition which further comprises 0.01-5 wt % of each of animal byproduct-derived threonine, animal byproduct-derived serine, animal byproduct-derived glycine, animal byproduct-derived valine, animal byproduct-derived isoleucine, animal byproduct-derived tyrosine, animal byproduct-derived phenylalanine, animal byproduct-derived histidine, animal byproduct-derived arginine, animal byproduct-derived proline, animal byproduct-derived methionine and animal byproduct-derived cysteine based on the total weight of the composition.

In another aspect of the present disclosure, the animal byproduct-derived amino acid composition may comprise each of threonine, serine, glycine, valine, isoleucine, tyrosine, phenylalanine, histidine, arginine, proline, methionine and cysteine in an amount of 0.01 wt % or more, 0.05 wt % or more, 0.1 wt % or more, 0.5 wt % or more, 1 wt % or more, 1.5 wt % or more, 2.0 wt % or more, 2.5 wt % or more, 3.0 wt % or more, 3.5 wt % or more, 4 wt % or more, 4.5 wt % or more, 5 wt % or more or 10 wt % or more or 10 wt % or less, 5 wt % or less, 4.5 wt % or less, 3.5 wt % or less, 4 wt % or less, 3.5 wt % or less, 3 wt % or less, 2.5 wt % or less, 2 wt % or less, 1.5 wt % or less, 1 wt % or less, 0.5 wt % or less, 0.1 wt % or less, 0.05 wt % or less or 0.01 wt % or less based on the total weight of the composition. Specifically, it may comprise each of threonine, serine, glycine, valine, isoleucine, tyrosine, phenylalanine, histidine, arginine, proline, methionine and cysteine in an amount of 0.1-2 wt %. More specifically, it may comprise 0.85 wt % of threonine, 1.01 wt % of serine, 0.98 wt % of glycine, 1.32 wt % of valine, 0.12 wt % of isoleucine, 0.58 wt % of tyrosine, 1.4 wt % of phenylalanine, 1.35 wt % of histidine, 0.83 wt % of arginine, 0.92 wt % of proline, 0.16 wt % of methionine and 0.26 wt % of cysteine.

In an aspect of the present disclosure, the product may comprise one or more of a fertilizer, a feed additive and a food additive.

In an aspect of the present disclosure, the product may be in the form of one or more of a liquid, a powder and a pellet, although not being limited thereto.

In an aspect of the present disclosure, the feed that can be prepared by applying the present disclosure is not limited in type. It may be applied to any type of feed that can be supplied to animals, including livestock, pets and aquacultured fish. And, the feed additive may further comprise an acceptable carrier. In the present disclosure, the feed additive may be used as it is or after adding a known carrier, stabilizer, etc. If necessary, various nutrients such as vitamins, amino acids, minerals, etc. and other additives such as an antioxidant, an antibiotic, an antibacterial agent, etc. may be used. The feed additive may be in a suitable form such as a liquid, a powder, a granule, a pellet, a suspension, etc. The feed additive of the present disclosure may be supplied either alone or as mixed with a feed.

The addition amount of the amino acid composition of the present disclosure in a feed is not specially limited. In an aspect of the present disclosure, when the composition is in the form of a liquid, it may be added in an amount of 0.01 wt % or more, 0.03 wt % or more, 0.08 wt % or more, 0.1 wt % or more, 0.2 wt % or more, 0.3 wt % or more, 0.4 wt % or more, 0.5 wt % or more, 0.6 wt % or more, 0.7 wt % or more, 0.8 wt % or more, 0.9 wt % or more, 1.0 wt % or more, 1.5 wt % or more, 2.0 wt % or more, 2.5 wt % or more, 3.0 wt % or more, 5.0 wt % or more, 7.0 wt % or more, 10 wt % or more, 13 wt % or more or 15 wt % or more or 0.01 wt % or less, 0.03 wt % or less, 0.08 wt % or less, 0.1 wt % or less, 0.2 wt % or less, 0.3 wt % or less, 0.4 wt % or less, 0.5 wt % or less, 0.6 wt % or less, 0.7 wt % or less, 0.8 wt % or less, 0.9 wt % or less, 1.0 wt % or less, 1.5 wt % or less, 2.0 wt % or less, 2.5 wt % or less, 3.0 wt % or less, 5.0 wt % or less, 7.0 wt % or less, 10 wt % or less, 13 wt % or less or 15 wt % or less, specifically 0.1-0.3 wt %, based on the total weight of the feed.

And, when the amino acid composition of the present disclosure is in the form of a powder, it may be added in an amount of 0.01 wt % or more, 0.015 wt % or more, 0.1 wt % or more, 0.15 wt % or more, 0.2 wt % or more, 0.25 wt % or more, 0.3 wt % or more, 0.35 wt % or more, 0.4 wt % or more, 0.45 wt % or more, 0.5 wt % or more, 0.55 wt % or more, 0.6 wt % or more, 0.7 wt % or more, 0.8 wt % or more, 0.9 wt % or more, 1.0 wt % or more, 3.0 wt % or more, 5.0 wt % or more, 8.0 wt % or more or 10.0 wt % or more or 0.01 wt % or less, 0.015 wt % or less, 0.1 wt % or less, 0.15 wt % or less, 0.2 wt % or less, 0.25 wt % or less, 0.3 wt % or less, 0.35 wt % or less, 0.4 wt % or less, 0.45 wt % or less, 0.5 wt % or less, 0.55 wt % or less, 0.6 wt % or less, 0.7 wt % or less, 0.8 wt % or less, 0.9 wt % or less, 1.0 wt % or less, 3.0 wt % or less, 5.0 wt % or less, 8.0 wt % or less or 10.0 wt % or less, specifically 0.2-0.5 wt %, based on the total weight of the feed.

In an aspect of the present disclosure, there is no limitation in the food. Examples of the food to which the amino acid composition of the present disclosure can be added comprise drinks, meat, sausage, bread, biscuit, rice cake, chocolate, candy, snack, confectionery, pizza, instant noodle, other noodles, gums, dairy products including ice cream, soups, beverages, alcoholic beverages, vitamin mixtures, etc. Various indulgence foods, health foods, food supplements, health functional foods and food additives in common sense are comprised.

The amino acid composition of the present disclosure may be comprised in a food in an amount of 0.1 wt % or more, 0.2 wt % or more, 0.3 wt % or more, 0.4 wt % or more, 0.5 wt % or more, 0.6 wt % or more, 0.7 wt % or more, 0.8 wt % or more, 0.9 wt % or more, 1.0 wt % or more, 2.0 wt % or more, 3.0 wt % or more, 5.0 wt % or more, 1.0 wt % or more, 5.0 wt % or more, 10 wt % or more, 15 wt % or more, 20 wt % or more or 30 wt % or more or 0.1 wt % or less, 0.2 wt % or less, 0.3 wt % or less, 0.4 wt % or less, 0.5 wt % or less, 0.6 wt % or less, 0.7 wt % or less, 0.8 wt % or less, 0.9 wt % or less, 1.0 wt % or less, 2.0 wt % or less, 3.0 wt % or less, 5.0 wt % or less, 1.0 wt % or less, 5.0 wt % or less, 10 wt % or less, 15 wt % or less, 20 wt % or less or 30 wt % or less, specifically 0.5-1.0 wt %, based on the total weight of the food.

In an aspect of the present disclosure, the food additive comprising the amino acid composition may comprise other ingredients within a range not negatively affecting the effect desired by the present disclosure. For example, it may further comprise additives for improving physical properties, such as a flavor, a pigment, a sterilizer, an antioxidant, an antiseptic, a humectant, a thickener, a mineral, an emulsifier, a synthetic polymer, etc. In addition, it may further comprise auxiliary ingredients such as a water-soluble vitamin, an oil-soluble vitamin, a polypeptide, a polysaccharide, a seaweed extract, etc. These ingredients may be selected by those skilled in the art without difficulty depending on the particular formulation or purpose of use and the addition amount may be selected within a range not negatively affecting the purpose and effect of the present disclosure. For example, the addition amount of the ingredients may be 0.001-10 wt %, more specifically 0.001-5 wt %, based on the total weight of the composition.

In an aspect of the present disclosure, the formulation of the food additive comprising the amino acid composition is not specially limited. For example, it may be prepared into various forms such as a gum, a chewing gum, a solid, a semisolid, a tablet, a granule, a pellet, a powder, a liquid such as a drink, an emulsion, a viscous mixture, a caramel, a gel, a bar, etc. Each formulation may comprise, in addition to the active ingredient, ingredients commonly used in the art that may be selected by those skilled in the art without difficulty depending on the particular formulation or purpose of use. In this case, a synergic effect may be achieved.

In addition, the food additive according to an aspect of the present disclosure may comprise various nutrients, vitamins, minerals (electrolytes), flavors such as synthetic and natural flavors, colorants, extenders, pectic acid and salts thereof, alginic acid and salts thereof, organic acids, protective colloidal thickeners, pH control agents, stabilizers, antiseptics, glycerin, alcohols, carbonating agents used in carbonated drinks, etc. In addition, the food additive of the present disclosure may comprise pulp for preparing natural fruit juice, fruit juice drink and vegetable drink. These ingredients may be used either independently or in combination. In general, the addition amount of these additional ingredients is about 0-80 parts by weight based on 100 parts by weight of the food additive of the present disclosure although it is of no significant importance.

Hereinafter, the present disclosure will be described in detail through examples, a comparative example and preparation examples. However, the following examples are for illustrative purposes only and it will be apparent to those of ordinary skill in the art that the scope of the present disclosure is not limited by them.

EXAMPLE 1

Removal of Cell Membrane from Sample

In order to maximize the contact surface area between an enzyme and a substrate, maintain a weakly acidic condition under which the enzyme can function properly and maintain an optimum temperature condition under which proteins can be more easily degraded into amino acids, cell membrane was removed from the substrate as follows.

<1-1> Preparation and Crushing of Blood Sample

A blood sample was crushed to maximize the contact surface area between an enzyme and a substrate, thereby achieving the maximum effect of the enzyme.

Specifically, cow blood was acquired from a slaughterhouse as a byproduct. Before crushing, some of the blood was kept at 5-7° C. and some was kept at −20° C. or lower.

Figure 1:
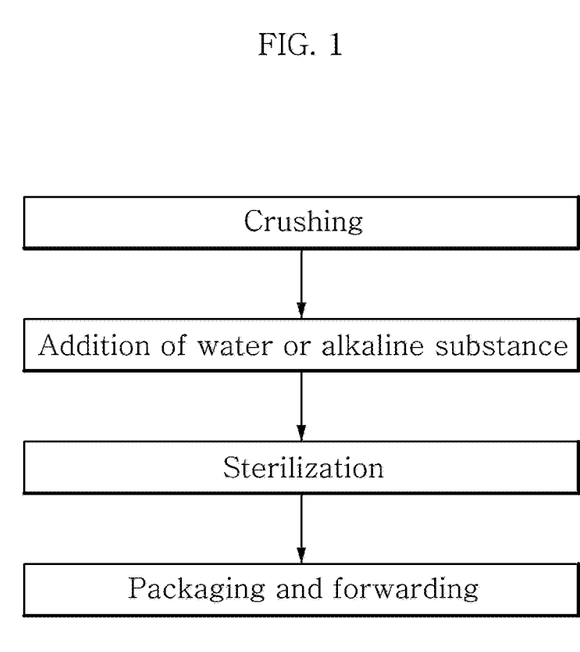
FIG. 1 schematically describes a process of preparing an amino acid composition of the present disclosure.
Figure 2:
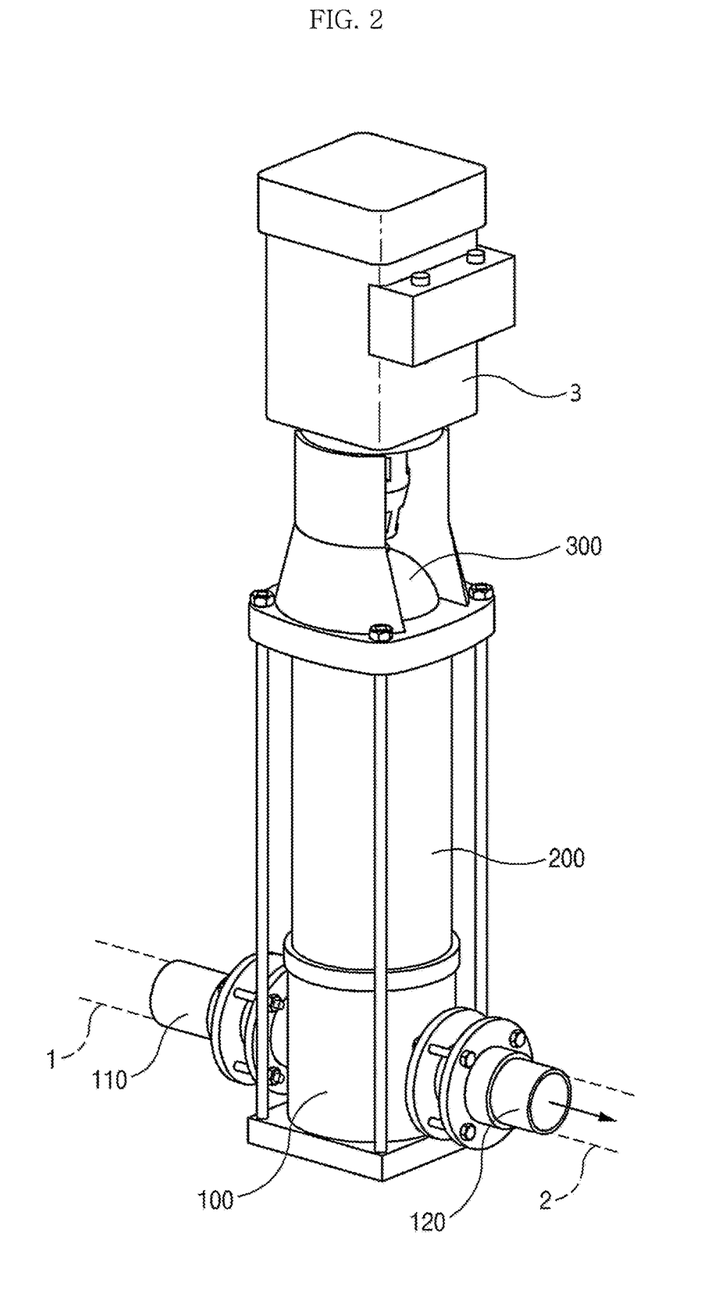
FIG. 2 is a perspective view of a nanobubble generator according to an exemplary embodiment of the present disclosure (1: inlet pipe, 2: outlet pipe, 3: motor, 100: base, 110: inlet, 120: outlet, 200: outer sleeve, 300: head).
Figure 3:
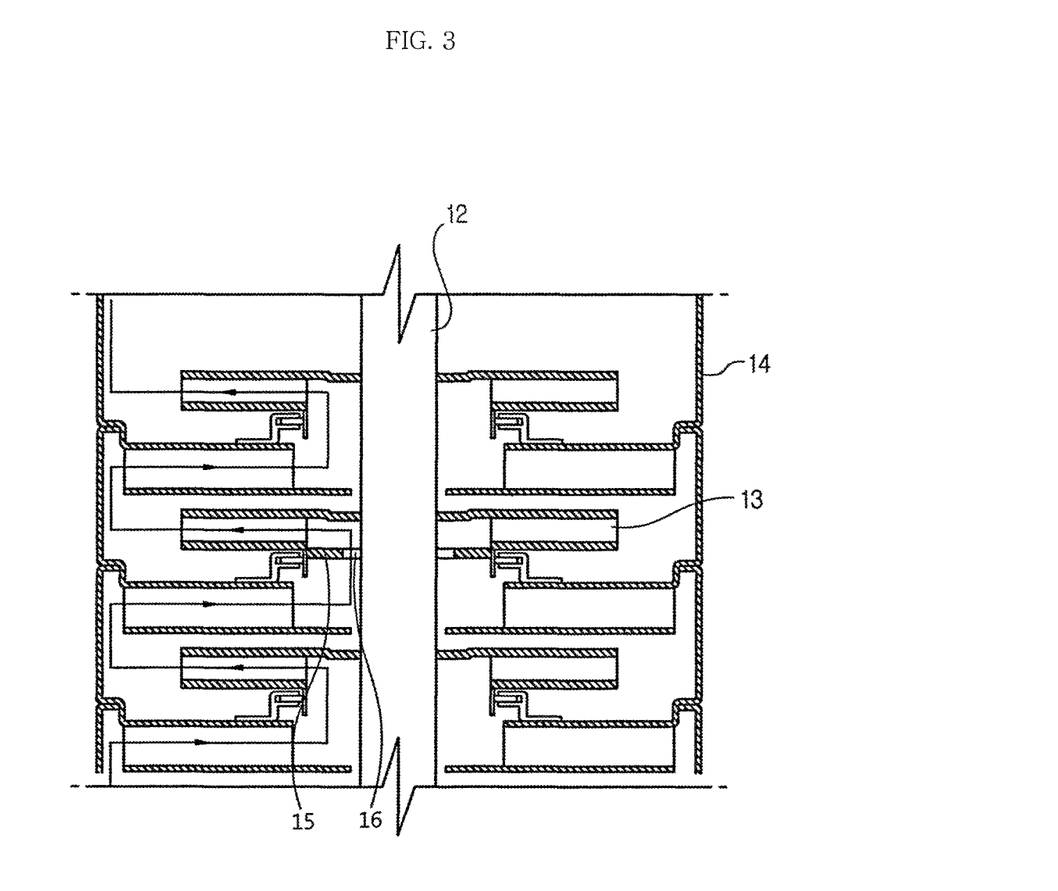
FIG. 3 is a cross-sectional view of a vertical multi-stage part of a nanobubble generator according to another exemplary embodiment of the present disclosure (12: rotary shaft, 13: circular impeller, 14: lock chamber, 15: pressure plate, 16: discharge space, the arrow indicates the direction of fluid flow).

Then, 350 g of the blood was added to a nanobubble generator and crushed for a predetermined time (0.5-1 hour). The nanobubble generator was an apparatus which can move a liquid from a lower pressure to a higher pressure. The apparatus can comprise a motor which generates driving force using electricity, an impeller which rotates by the driving force of the motor and moves a liquid and a coupler which connects a shaft of the motor to the impeller. When a plurality of impellers are used to provide a stronger pressure, an apparatus with a vertical multi-stage structure may be used. The nanobubble generator used in this example (diameter: 32-125 mm, maximum capacity: 250 $m^2$/h, maximum allowable pressure: 30 bar, power: 0.75-100 kW, bubble size: average diameter ≤1 μm) was an apparatus with a vertical multi-stage structure which is commercially available. It is schematically shown in FIG. 2 and FIG. 3.

In the present disclosure, the nanobubble generator described above or an apparatus with a better specification may be used. FIG. 2 shows the external appearance of the nanobubble generator and the FIG. 3 shows the cross-sectional view of the portion where circular impellers that generate nanobubbles are provided in multiple stages.

The nanobubble generator is an important apparatus for crushing blood by generating nanobubbles and may be equipped with circular impellers with a vertical multi-stage structure. The circular impeller may have projections for generating turbulence, cavitation, air bubbling etc. Of the circular impellers of different types shown in FIG. 4 (perspective views, plan views and side views of circular impellers of three types), type 3 was found to provide the highest fermentation efficiency. Therefore, type 3 was used in this example.

Figure 4:
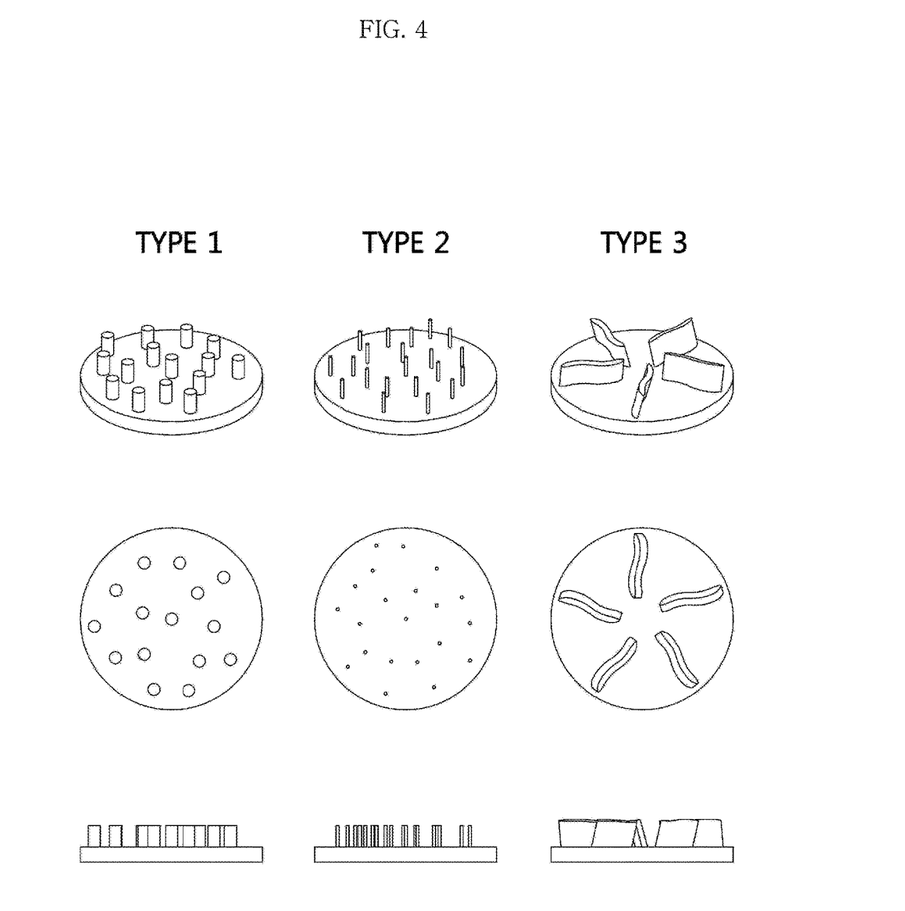
FIG. 4 shows circular impellers of different types that may be used in a nanobubble generator according to an exemplary embodiment of the present disclosure.

FIG. 4 shows circular impellers of different types that may be used in a nanobubble generator according to an exemplary embodiment of the present disclosure.

When the time required for fermentation using the nanobubble generator was measured, it was found out that the fermentation time was remarkably decreased to 3.5 hours or shorter whereas it took longer than 9 hours under the same fermentation condition when the existing mechanical crushing apparatus (a mechanical crushing apparatus equipped with a stainless steel (STS304) rotary propeller) was used. Details are given in Tables 2 and 3.

Then, the cell membrane was removed based on the principle of osmosis by adding water. The efficiency was the highest when the amount of the water was about 10% of the sample amount. In this example, 35 g of water was added to 350 g of the sample. The water was not purified water but purified water to which an alkaline substance has been added (prepared by adding 10% of NaOH or KOH based on the weight of purified water) or lye prepared using wood ash (ash powder of deciduous or coniferous tree) (prepared by adding 10 wt % of ash powder based on the weight of purified water and extracting for about 10 days). When lye prepared from wood ash is used, the function and effect of the final product are improved due to the mineral ingredients extracted from the ash powder.

<1-2> Determination of pH and Temperature Conditions

The optimum pH and temperature conditions under which the cell membrane can be effectively removed from the sample and the enzyme can function properly were determined.

Specifically, it was found out that it is desired that pH be maintained around 5.9 to prevent the denaturation of amino acids and to effectively remove the cell membrane.

Also, measures to weaken protein binding and easily convert the same to amino acids were investigated. In order to weaken protein binding, (1) heating, (2) high-frequency treatment, (3) electrolysis, (4) addition of an acid and (5) freezing were considered. The high-frequency treatment was not so effective because the effect was exerted only up to the shallow depth of the protein. The electrolysis and addition of an acid were problematic in that conversion efficiency to amino acids was very low due to denaturation of protein. As a consequence, it was found out that (1) heating and (5) freezing are suitable methods to weaken protein binding without denaturation of amino acids.

Because an enzyme is used for fermentation, the temperature at which the enzyme exerts the optimum effect was considered. It was found out that the optimum temperature for the enzyme used in an aspect of the present disclosure was 52-65° C. and the maximum effect was exerted at 65° C. It was important that maintaining the temperature at 65° C. It was also found out that, at temperatures above 65° C., the blood is hardened due to denaturation of amino acids and stirring and fermentation are impossible.

EXAMPLE 2

Fermentation, Stirring and Preservation of Sample

The sample obtained in <1-1> of Example 1 was fermented by adding 13.5 g of an enzyme.

The following enzymes were used.

TABLE 1

| Manufacturer | Product Name | Function |
|---|---|---|
| (1) NEC (National Enzyme Company) | Gluten Digest | Proteinase |
| (2) NEC (National Enzyme Company) | INNATE | Proteinase mixture |
| (3) Vision Biochem | Papain T100 | Plant protease |
| (4) Vision Biochem | Actinidin | Proteinase |
| (5) Great Food Biochem | Bromelain 12poGDU | Proteinase |
| (6) Insect Biotech | Metallo-protease | Proteinase |
| (7) K-Therapeutics | Florazyme | Proteinase mixture |

Because different enzymes can be used depending on the substrate pH and it was found out that the substrate comprising proteins (blood, guts, etc.) has initially an acidic pH, it was confirmed that it is effective to make a weakly acidic condition by mixing with the alkaline substance or lye as in <1-1> in order to ensure effective removal of the cell membrane and aid in enzymatic action.

That is to say, it was confirmed that amino acid extraction can be achieved in short time by preparing a weakly acidic condition of pH 5-7.5 and then adding a mixture of enzymes that act effectively in this pH range. It was confirmed that, at low temperature (20-30° C.), addition of the enzymes (3) and (4) (weight ratio=1:1) is effective and the enzymes can be used regardless of the freshness of the sample. At high temperature (52-65° C.), it was confirmed that fermentation can be performed effectively by using a mixture of the enzymes (1), (5) and (7) (weight ratio=1:1:1) when the sample was maintained fresh within one day after slaughter. When moderate freshness was maintained (2-3 days after slaughter), it was confirmed that fermentation can be performed effectively by using a mixture of the enzymes (1), (2) and (6) (weight ratio=1:1:1). After 4 days, when fermentation was not performed effectively by using a mixture of the enzymes (1), (2) and (6) (weight ratio=1:1:1), it was confirmed that fermentation can be performed effectively by using a mixture of the enzymes (1), (5) and (7) (weight ratio=1:1:1, 3.5% based on total weight).

In the mixtures, the enzymes were added with the same weight, with a constant ratio based on the total weight of the sample, as shown in Table 2 and Table 3.

In order to enhance fermentation efficiency, the resulting mixture was stirred at a constant rate after the addition of the enzymes. The result is shown in Table 3.

After the fermentation was completed, the activity of the enzymes was inhibited through sterilization. If the enzymes remain activated after the fermentation is completed, offensive odor may be generated as ammonia is produced from the reaction between the amino group ($-NH_2$) and hydrogen. Therefore, it is desired to inhibit the enzymatic activity to avoid such a reaction. Heating may be performed to inhibit the enzymatic activity. The enzymatic activity may be inhibited by heating at 70-80° C. for 1 minute. Alternatively, the enzymatic activity may be inhibited through sterilization. In this example, the enzymatic activity was inhibited through strong sterilization by hydroxyl (OH) groups by mixing with ozone.

In addition, for long-term preservation of the fermented sample, 19.3 g of a preservative solution prepared by mixing a solution of 2% of mugwort, plantain, aloe, peony and grapefruit based on the weight of purified water extracted by heating with wood vinegar (prepared by condensing steam generated during carbonization of wood; easily commercially available) at a weight ratio of 1:1 was added.

COMPARATIVE EXAMPLE 1

Fermentation Time Depending on Enzyme Addition Time, Heating Time, Stirring Rate, Etc.

The time until fermentation was completed was measured while varying the sample temperature before the addition of enzymes, the time when enzyme was added, the time when temperature reached 65° C., and the stirring rate. The result is shown in Table 3.

From Table 3, it can be seen that, as compared to when the sample was crushed by the existing mechanical crushing method and fermentation was performed using 1.93 g or 0.5 wt % of the enzyme based on 385 g of the sample (350 g of blood+35 g of alkaline substance-comprising purified water or lye) by stirring at a rate of 45 rpm (Ex. 1), the fermentation time was decreased from 7 hours to 6 hours when 3.5% (13.5 g) of the enzyme was used based on the total weight (385 g) of the sample to which the alkaline substance-comprising purified water or lye was added and fermentation was conducted at a stirring rate of 60 rpm (Ex. 1-1). The completion of fermentation can be ascertained by precipitation. If, when the fermented sample is boiled and purified water is added, the sample is dissolved homogeneously in the purified water without precipitation, it means that the fermentation has been completed. If the fermentation has not been completed, the sample is not dissolved homogeneously in the purified water and precipitation occurs or powder remains on the surface of the sample.

Also, it can be seen from Table 3 that the fermentation time was decreased from 6 hours to 5 hours and 5 minutes when the time for heating the sample to 65° C. was 30 minutes (Ex. 1-2) as compared to when it was 1 hour (Ex. 1-1).

It can also be seen that the fermentation time can be remarkably decreased by crushing the sample using a nanobubble generator, adding the enzyme and then raising the temperature to 65° C. (Ex. 2, Ex. 3-1 and Ex. 3-2) as compared to when the sample was crushed by mechanical crushing and the enzyme was added after raising the temperature to 65° C. (Ex. 1, Ex. 1-1 and Ex. 1-2). In this case, the fermentation time could be further decreased when the stirring rate was 60 rpm as compared to when it was 90 rpm (Ex. 3-1 and Ex. 3-2).

When the sample was frozen at −25° C. for 5 hours without adding the alkaline substance-comprising purified water or lye and fermented after crushing (Ex. 4), the fermentation time was slightly increased.

EXAMPLE 3

Non-Blood Samples

It was investigated whether the present disclosure can be applied also to animal guts.

<3-1> Pig Liver 2 kg of commercially available pig liver was crushed finely with a blender and then mixed with 2 kg of water. Sample A and sample B were prepared respectively by adding 1.5 kg of the mixture with 1.5 kg of water. Sample C was prepared by mixing 600 g of the mixture with 600 g of purified water to which the alkaline substance of <1-1> was added.

Samples A, B and C were fermented in the same manner as in the examples and comparative example. For sample A, an enzyme was added as soon as the sample was prepared as described above. For sample B and sample C, the enzyme was added when the temperature reached 58° C. Then, fermentation was conducted while maintaining the temperature at 58° C. It was confirmed that fermentation was completed for sample C only. Details are given in the following table.

TABLE 2

| | Sample crushing method | Enzyme (g) | Temperature before enzyme addition (° C.) | Stirring rate (rpm) | Time when sample was completed before enzyme addition (hh:mm) | Time when enzyme was added (hh:mm) | Time when temperature reached 52° C. (hh:mm) | Time when fermentation was completed (hh:mm) | Fermentation time |
|---|---|---|---|---|---|---|---|---|---|
| Existing method | Mechanical | 1.93 | 21 | 45 | 13:09 | 14:42 | 14:42 | 23:30 | 10 hr 21 min |

TABLE 3

| | Sample crushing method | Enzyme (g) | Temperature before enzyme addition (° C.) | Stirring rate (rpm) | Time when sample was completed before enzyme addition (hh:mm) | Time when enzyme was added (hh:mm) | Time when temperature reached 65° C. (hh:mm) | Time when fermentation was completed (hh:mm) | Fermentation time |
|---|---|---|---|---|---|---|---|---|---|
| Ex. 1 | Mechanical | 1.93 | 21 | 45 | 10:15 | 12:11 | 12:11 | 17:15 | 7 hr |
| Ex. 1-1 | Mechanical | 13.5 | 20 | 60 | 09:15 | 10:15 | 10:15 | 15:15 | 6 hr |
| Ex. 1-2 | Mechanical | 13.5 | 21 | 60 | 15:15 | 15:45 | 15:45 | 20:20 | 5 hr 5 min |
| Ex. 2 | Nanobubble | 13.5 | 21 | 60 | 16:30 | 16:47 | 18:00 | 20:00 | 3 hr 30 min |
| Ex. 3-1 | Nanobubble | 13.5 | 20 | 60 | 20:32 | 20:32 | 21:55 | 23:45 | 3 hr 13 min |
| Ex. 3-2 | Nanobubble | 13.5 | 21 | 90 | 09:32 | 09:32 | 11:00 | 13:10 | 3 hr 38 min |
| Ex. 4 | Nanobubble | 13.5 | Frozen for 5 hours (−20° C.) | 60 | 13:50 | 15:25 | 17:25 | 19:30 | 5 hr 40 min |

TABLE 4

|  | Enzyme (g) | Time when sample was prepared (hh:mm) | Stirring rate (rpm) | Time when enzyme was added (hh:mm) | Sample temperature when enzyme was added (° C.) | Time when fermentation was completed (hh:mm) |
|---|---|---|---|---|---|---|
| Sample A | 13.5 | 15:15 | 60 | 15:15 | 10 | 09:00, next day |
| Sample B | 13.5 | 15:15 | 60 | 17:05 | 58 | 09:00, next day |
| Sample C | 13.5 | 15:15 | 60 | 17:30 | 58 | 09:00, next day |

<3-2> Pig Heart 2.2 kg of commercially available pig heart was crushed finely with a blender and then mixed with 4 kg of water. After filtering off impurities, 2.5 L of the resulting mixture was mixed with 1 L of water.

Sample A and sample B were prepared in this manner and the two samples were fermented in the same manner as in the examples and comparative example. An enzyme was added as soon as the samples were prepared. For sample B, 5 wt % of purified water to which the alkaline substance of <1-1> was added was added.

During the stirring of sample A, a significant amount of lumpy substance such as tendon was formed, which was removed. The temperature of sample B was raised to 64° C. and maintained at 68° C. The two samples were filtered through a 200-mesh filter and stored at 5° C.

The enzyme was added at 13:44 and the fermentation was completed at 09:00 on the next day.

<3-3> Mixture of Cow Liver and Pig Liver 11.2 kg of commercially available cow liver and 8.9 kg of commercially available pig liver were crushed finely with a blender and water was added. 22.4 kg of a sample was prepared for the cow liver and 17.8 kg of a sample was prepared for the pig liver, which were crushed again with a nanobubble generator. After removing 2 kg from each sample, the two samples were mixed.

The mixed 36.2 kg sample was fermented by adding an enzyme and stirring. The result is shown in the following table.

TABLE 5

|  | Enzyme (g) | Time when sample was prepared (hh:mm) | Stirring rate (rpm) | Time when enzyme was added (hh:mm) | Sample temperature when enzyme was added (° C.) | Time when temperature reached 58° C. (hh:mm) | Time when fermentation was completed (hh:mm) |
|---|---|---|---|---|---|---|---|
| Mixture sample | 13.5 | 14:48 | 60 | 14:48 | 10 | 16:34 | 20:38 |

<3-4> Comparison of Cow Liver and Pig Liver 6 kg of commercially available cow liver and 2 kg of commercially available pig liver were crushed finely with a blender and a 12 kg sample was prepared for the cow liver and a 4 kg sample was prepared for the pig liver by adding 6 kg and 2 kg of water, respectively. The samples were crushed again with a nanobubble generator.

1.5 L of each sample was fermented by adding an enzyme and stirring. The result is shown in the following table.

TABLE 6

|  | Enzyme (g) | Time when sample was prepared (hh:mm) | Stirring rate (rpm) | Time when enzyme was added (hh:mm) | Sample temperature when enzyme was added (° C.) | Time when temperature reached 58° C. (hh:mm) | Time when fermentation was completed (hh:mm) |
|---|---|---|---|---|---|---|---|
| Cow liver sample | 13.5 | 15:10 | 60 | 15:15 | 10 | 16:54 | 20:10 |
| Pig liver sample | 13.5 | 15:10 | 60 | 15:15 | 10 | 16:54 | 20:10 |

<3-5> Comparison of Cow Liver and Pig Liver (when Alkaline Substance-Comprising Purified Water was Added)

1.5 kg of commercially available cow liver and 1.5 kg of commercially available pig liver were crushed finely with a blender and 1.65 kg samples were prepared respectively by adding 0.15 kg of water. After adding 20 wt % of the alkaline substance-comprising purified water of <1-1> to each sample, the sample was crushed again with a blender.

The samples were fermented by adding an enzyme and stirring. The result is shown in the following table.

TABLE 7

| | Enzyme (g) | Time when sample was prepared (hh:mm) | Stirring rate (rpm) | Time when enzyme was added (hh:mm) | Sample temperature when enzyme was added (° C.) | Time when temperature reached 58° C. (hh:mm) | Time when fermentation was completed (hh:mm) |
|---|---|---|---|---|---|---|---|
| Cow liver sample | 13.5 | 09:24 | 60 | 09:24 | 10 | 11:01 | 14:42 |
| Pig liver sample | 13.5 | 09:24 | 60 | 09:24 | 10 | 11:01 | 14:42 |

PREPARATION EXAMPLE 1

Preparation of Fertilizer

Proteins are applicable as various products after being converted to amino acids. They can be used for fertilizers, feeds and food additives and can be prepared into liquid, powder or pellet form.

Various liquid fertilizer products can be produced by adding various nutrients to amino acids produced from the amino acid compositions according to the examples and comparative example. The products can be used for soil fertilization or foliar feeding by mixing with water.

<1-1> Basic Liquid Fertilizer

Category 4 compound fertilizers were prepared by adding water-soluble nitrogen (N), phosphorus (P), potassium (K), copper (Cu), boron (B), etc. to the amino acid compositions according to the examples and comparative example.

<1-2> Concentrated Amino Acid Liquid Fertilizer

Concentrated fertilizers were prepared by increasing the amino acid content of the basic liquid fertilizers. Specialized products for root crops, roots, flowers, dwarf trees, sod, etc. can also be produced by adding minerals and trace elements such as potassium (K), calcium (Ca), silicon (Si), etc.

<1-3> High-Quality Liquid Fertilizer

High-quality liquid fertilizers were prepared by adding minerals and functional ingredients resistant to harmful insects to the basic liquid fertilizers.

The functional ingredient may be, for example, a loess-sulfur mixture. The loess-sulfur mixture may be prepared by dissolving 10 wt % of sulfur, 10 wt % of salt, 10 wt % of loess and 10 wt % of caustic soda based on the total weight of the mixture in water to make a final volume 64 L and then further adding 36 L of water 2-3 days later.

<1-4> Pellet-Type Fertilizer

A pellet-type fertilizer which can be sprayed directly to soil was prepared by impregnating the liquid product in a vehicle. The vehicle may be one or more selected from rice bran, corn, barley, wheat and rice.

A pellet-type fertilizer was also prepared by absorbing the liquid amino acid composition into wood and preparing the wood into a pellet shape using tar which acts as an adhesive. The pellet-type fertilizer is variously applicable to roadside trees, landscaping trees, dwarf trees, etc. because it is absorbed slowly when sprayed onto soil.

PREPARATION EXAMPLE 2

Preparation of Feed Adjuvant or Feed Additive

<2-1> Liquid Feed Adjuvant or Feed Additive

A liquid feed adjuvant or feed additive that can be provided to animals was prepared by mixing 0.1-0.3 wt % of the amino acid composition according to the examples or comparative example with a feed (corn, compound feed, etc.) based on the total weight of the feed.

<2-2> Powder (Including Pellet Form)

After preparing the amino acid composition according to the examples or comparative example into powder by low-temperature vacuum drying, freeze-drying, hot air drying, etc., a powder- or pellet-type feed adjuvant or feed additive was prepared by mixing 0.2-0.5 wt % of the powder based on the total weight of a feed. The feed adjuvant or feed additive can be further processed to satisfy legal requirements or standards.

Because hot air drying is associated with the concern that the active ingredient may be damaged due to oxidation, low-temperature vacuum drying is more desirable to prepare a powder- or pellet-type product in that the active ingredient can be preserved with little damage and production cost is low.

PREPARATION EXAMPLE 3

Preparation of Food Additive or Food Adjuvant

<3-1> Liquid Food Additive or Food Adjuvant 0.5-1.0 wt % of the amino acid composition according to the examples or comparative example may be added to food to effectively improve nutrition. In this case, the composition of the food can be controlled or the food can be further processed to satisfy the requirements or standards of the Food Sanitation Act and the Korean Food Code.

<3-2> Powder Food Additive or Food Adjuvant

The amino acid composition according to the examples or comparative example may be prepared into powder by low-temperature vacuum drying, freeze-drying, hot air drying, etc. to be added to food.

Because hot air drying is associated with the concern that the active ingredient may be damaged due to oxidation, low-temperature vacuum drying is more desirable to prepare a powder-type product in that the active ingredient can be preserved with little damage and production cost is low.

<3-3> Mixing with Rice Bran, Barley, Wheat, Rice, Corn, Etc.

0.5-1.0 wt % of the amino acid composition according to the examples or comparative example may be added to rice bran, barley, wheat, rice, corn, etc. to supply essential amino acids necessary for human.

DETAILED DESCRIPTION OF MAIN ELEMENTS

1: inlet pipe
2: outlet pipe
3: motor
100: base
110: inlet
120: outlet
200: outer sleeve
300: head
12: rotary shaft
13: circular impeller
14: lock chamber
15: pressure plate
16: discharge space

What is claimed is:

1. A method for preparing an amino acid composition using an animal byproduct, comprising:
   (1) disrupting the cell membrane of an animal byproduct;
   (2) obtaining a fermentation product by fermenting the byproduct with the cell membrane disrupted; and
   (3) sterilizing the fermentation product;
wherein disrupting the cell membrane in (1) comprises, in order:
   crushing the animal byproduct with a nanobubble generator that generates bubbles having an average diameter of less than 1 µm,
   adding purified water comprising an alkaline substance or adding lye prepared from wood ash, and
   controlling pH at 5-7 and temperature at 62-65° C.,
wherein obtaining the fermentation product in (2) comprises:
   mixing the cell membrane disrupted with two or more enzymes selected from pepsin, rennin, trypsin, chymotrypsin, erepsin, aminopeptidase, prolinase, prolidase, enterokinase, carboxypeptidase, dipeptidase, papain, bromelain, ficin, actinidain, elastase, subtilisin, pancreatin, nattokinase, arazyme, collagenase, keratinase, gelatinase, savinase, and subclasses thereof at a pH of 5-7,
   stirring the byproduct to which the enzymes have been added at 50-70 rpm, and
   controlling the temperature of the byproduct to which the enzymes have been added at a temperature of 61-65° C. after mixing with the enzymes, and
wherein sterilizing in (3) comprises sterilizing with ozone.

2. The method for preparing an amino acid composition according to claim 1, wherein the animal byproduct in (1) comprises the skin, muscle, blood, guts and placenta of livestock or fish.

3. The method for preparing an amino acid composition according to claim 1, wherein an amount of the purified water comprising an alkaline substance or the lye prepared from wood ash is 5-15 wt % based on the total weight of the byproduct.

4. The method for preparing an amino acid composition according to claim 1, wherein an amount of the enzyme is 2.5-4.5 wt % based on the total weight of the byproduct which has passed (1) of claim 1.

5. The method for preparing an amino acid composition according to claim 1, wherein said mixing is performed under a condition where the temperature of the byproduct which has passed (1) of claim 1 is 5-25° C.

6. The method for preparing an amino acid composition according to claim 1, which further comprises, after (3), adding a preservative.

7. The method for preparing an amino acid composition according to claim 6, wherein the preservative comprises a wood vinegar, and an extract obtained by extracting one or more selected from a group consisting of mugwort, plantain, aloe, peony and grapefruit, wherein the preservative is added in an amount of 3-7 wt % based on the total weight of the byproduct which has passed (1).

* * * * *